United States Patent [19]
Shinohara

[11] Patent Number: 5,694,446
[45] Date of Patent: Dec. 2, 1997

[54] X-RAY COMPUTED TOMOGRAPHY APPARATUS

[75] Inventor: Hisahiro Shinohara, Otawara, Japan

[73] Assignee: Kabushiki Kaisha Toshiba, Kawasaki, Japan

[21] Appl. No.: 642,346

[22] Filed: May 3, 1996

[30] Foreign Application Priority Data

May 10, 1995 [JP] Japan .................. 7-111920

[51] Int. Cl.$^6$ ...................................... A61B 6/03
[52] U.S. Cl. ........................................ 378/4; 378/19
[58] Field of Search .................. 378/4, 15, 19, 378/20

[56] References Cited

U.S. PATENT DOCUMENTS 5,513,237  4/1996  Nobuta et al. .................. 378/4 X

FOREIGN PATENT DOCUMENTS 7-194588  8/1995  Japan .

*Primary Examiner*—David P. Porta
*Attorney, Agent, or Firm*—Oblon, Spivak, McClelland, Maier & Neustadt, P.C.

[57] ABSTRACT

Projection data is repeatedly acquired by a helical scan operation. Tomographic image data is repeatedly reconstructed on the basis of projection data. Generally, in a helical scan operation, in order to reduce the artifact, interpolation processing of projection data is indispensable. Tomographic image is reconstructed on the basis of acquired original projection data without performing this interpolation processing so as to meet the condition that the time required to reconstruct tomographic image data on the basis of one set of projection data required for the reconstruction of tomographic image data be shorter than that required to acquire one set of projection data. The real-time mode can therefore be introduced into a helical scan operation.

9 Claims, 5 Drawing Sheets

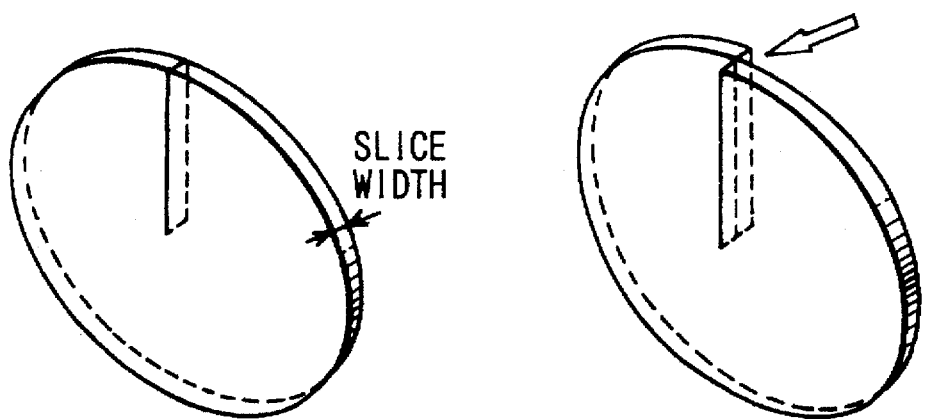
FIG. 1 (PRIOR ART)
FIG. 2 (PRIOR ART)
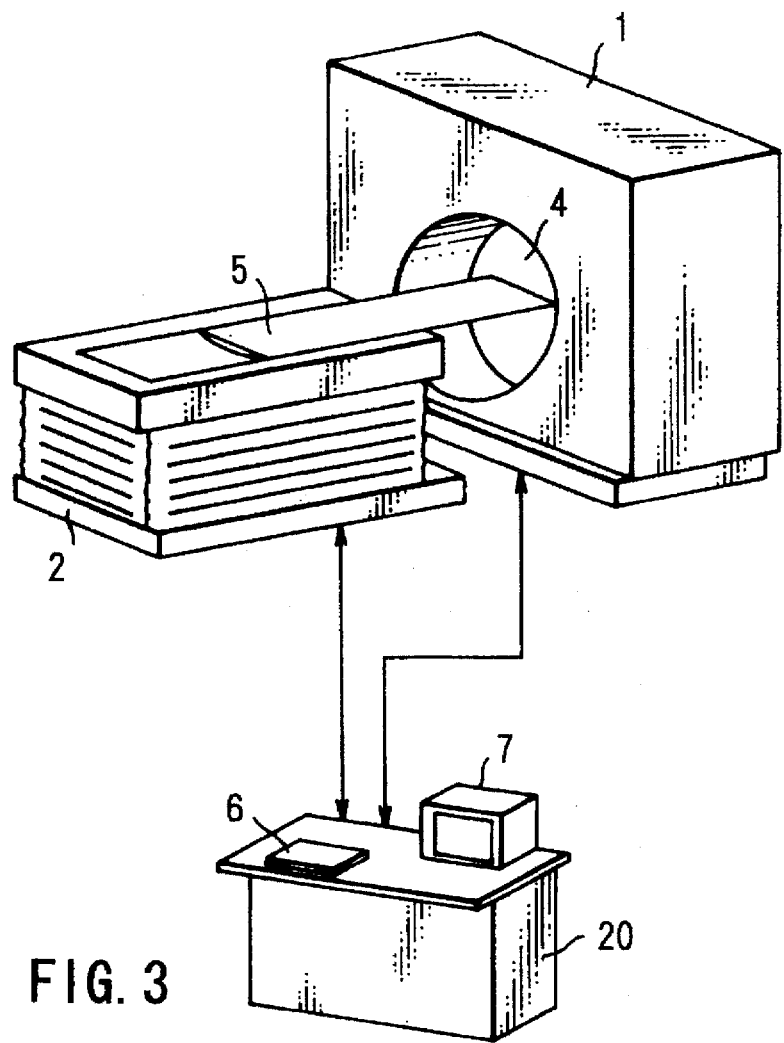
FIG. 3

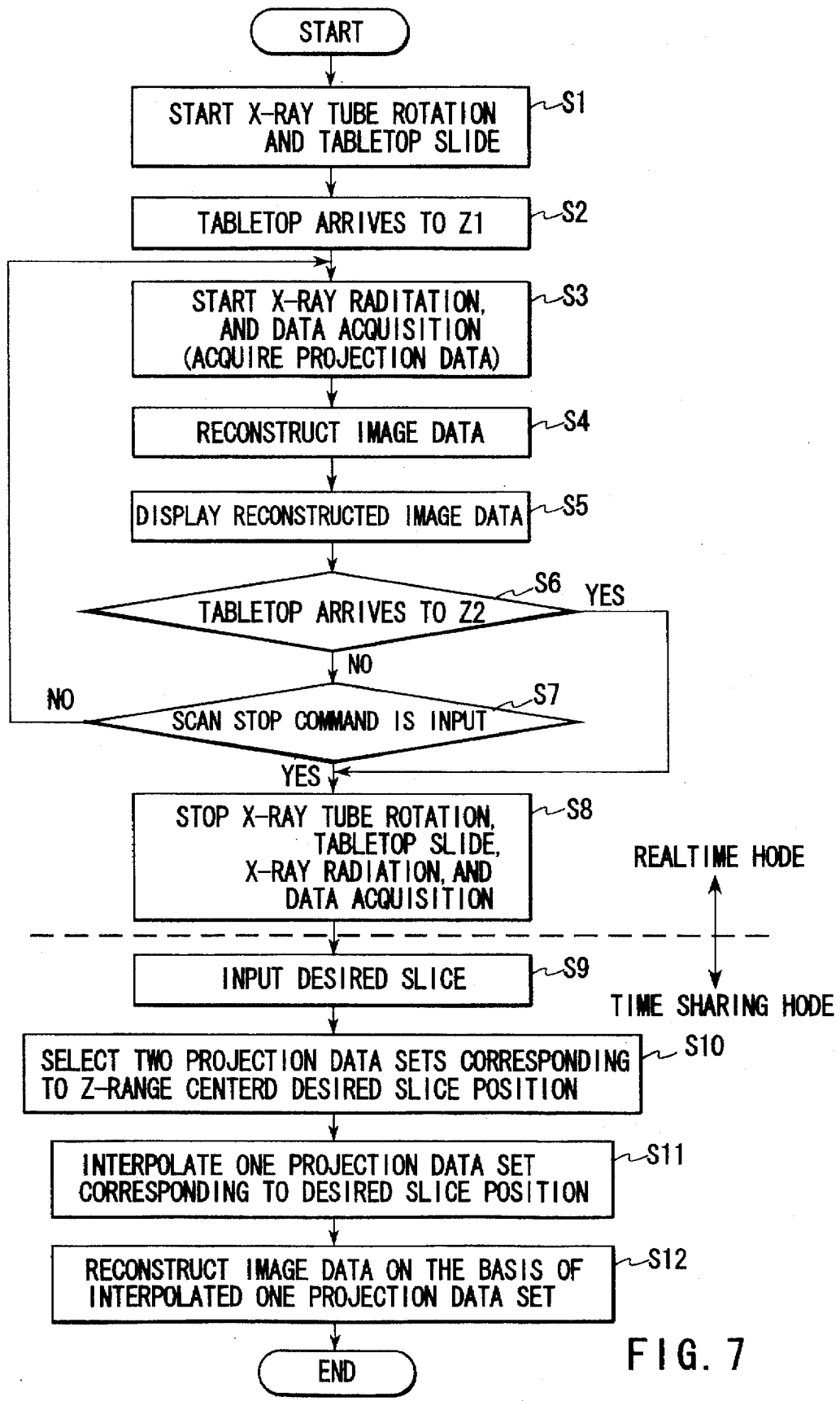
F I G. 7

X-RAY COMPUTED TOMOGRAPHY APPARATUS

BACKGROUND OF THE INVENTION

1. Field of the Invention

The present invention relates to an X-ray computed tomography apparatus capable of a helical scan operation.

2. Description of the Related Art

A helical scan operation is realized by continuously rotating an X-ray tube, a multi-channel type X-ray detector and a data acquisition unit, and the like in synchronism with sliding movement of the tabletop of a couch on which a subject is placed. The multi-channel type X-ray detector has an arcuated array of a plurality of detecting elements.

The X-ray tube moves on a helical orbit on the moving coordinate system of the subject. The acquisition unit repeats acquisition of projection data at a high speed.

FIG. 1 shows a slice obtained by a single scan operation. FIG. 2 shows a slice offset caused by a helical scan operation. In a helical scan operation, the Z-position changes every time projection data is acquired. In order to reconstruct tomographic image data corresponding to a slice position desired by an operator, projection data which approximates to the data acquired at the slice position must be interpolated from the actually acquired projection data (original projection data) for the following reason.

In order to reconstruct one-frame tomographic image data, a projection data set acquired during one rotation of the X-ray tube is required. This projection data set is a set of projection data having different Z-positions. If the projection data set having different Z-positions is used for reconstruction processing without interpolation, an artifact is caused by the Z-position differences.

The real-time mode which has recently been developed is an operation mode of reconstructing and displaying tomographic image data in real time while acquiring (scanning) projection data. A technical condition which is indispensable for realizing this real-time mode is that the time required to complete reconstruction of one-frame tomographic image data be shorter than that required to acquire a projection data set required for the reconstruction of one-frame tomographic image.

The time required for interpolation indispensable for a helical scan operation hinders the above technical condition from being met, and also precludes introduction of the real-time mode into a helical scan operation.

SUMMARY OF THE INVENTION

It is an object of the present invention to provide a computed tomography apparatus capable of introducing the real-time mode into a helical scan operation.

According to the present invention, provided to an X-ray computed tomography apparatus comprising:

acquisition means for repeatedly acquiring projection data associated with a subject by a helical scan operation;

reconstruction means for repeatedly reconstructing tomographic image data on the basis of the projection data, with a time required to reconstruct the tomographic image data on the basis of one set of projection data required for reconstruction of one-frame tomographic image data being shorter than a time required for acquisition of the one set of projection data; and display means for displaying the reconstructed tomographic image data as a moving image.

According to the present invention, provided to an X-ray computed tomography apparatus comprising:

acquisition means for repeatedly acquiring projection data associated with a subject by a helical scan operation;

reconstruction means capable of selecting a first mode of reconstructing tomographic image data on the basis of original projection data acquired by the acquisition means, and a second mode of interpolating the original projection data acquired by the acquisition means, and reconstructing tomographic image data on the basis of the interpolated projection data, and in the first mode, a time required to reconstruct the tomographic image data on the basis of one set of projection data required for reconstruction of one-frame tomographic image data being shorter than a time required for acquisition of the one set of projection data; and display means for displaying the reconstructed tomographic image data as a moving image.

The present invention has the following function. Projection data is repeatedly acquired by a helical scan operation. Tomographic image data is repeatedly reconstructed on the basis of the projection data, and is displayed as a moving image. Generally, in a helical scan operation, in order to reduce the artifact, interpolation processing of projection data is indispensable. According to the present invention, tomographic image data is reconstructed on the basis of acquired original projection data without performing this interpolation processing, thereby meeting the condition that the time required to reconstruct tomographic image data on the basis of one set of projection data required for the reconstruction of tomographic image data be shorter than that required to acquire one set of projection data. The real-time mode can therefore be introduced into a helical scan operation.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIG. 1 is a view showing a slice obtained by a single scan operation;

FIG. 2 is a view showing a slice offset caused by a helical scan operation;

FIG. 3 is a perspective view showing the outer appearance of a computed tomography apparatus according to a preferred embodiment of the present invention;

FIG. 7 is a flow chart showing the operation of the computer unit in FIG. 3;

DETAILED DESCRIPTION OF THE PREFERRED EMBODIMENTS

A preferred embodiment of the present invention will be described below.

Note that computed tomography apparatuses include various types of apparatuses, e.g., a rotate/rotate-type apparatus in which an X-ray tube and a multi-channel type X-ray detector rotate together, and a stationary/rotate-type apparatus in which many detecting elements are aligned in a ring array, and only an X-ray tube rotates. This embodiment will exemplify the rotate/rotate-type apparatus. However, it does not mean that the present invention cannot be applied to other types.

In order to reconstruct one-frame tomographic image data, projection data repeatedly acquired during almost one revolution of the X-ray tube or during almost ½ revolution thereof is required. Consider the former case. That is, one-frame tomographic image data is reconstructed on the basis of projection data acquired during one revolution of the X-ray tube. This, however, does not mean that the latter case cannot be employed.

A set of projection data required for reconstruction of one-frame tomographic image data and repeatedly acquired during one revolution of the X-ray tube is defined as a projection data set.

A scan operation is defined as an operation of repeatedly acquiring projection data at a predetermined angular pitch while rotating the X-ray tube around a subject. A helical scan operation is defined as an operation of repeatedly acquiring projection data at a predetermined pitch on the helical orbit of the X-ray tube, viewed from the subject, which is formed when rotation (revolution) of the X-ray tube around the subject occurs concurrently with movement of at least one of a tabletop, on which the subject is placed, and the X-ray relative to the other.

Figure 4:
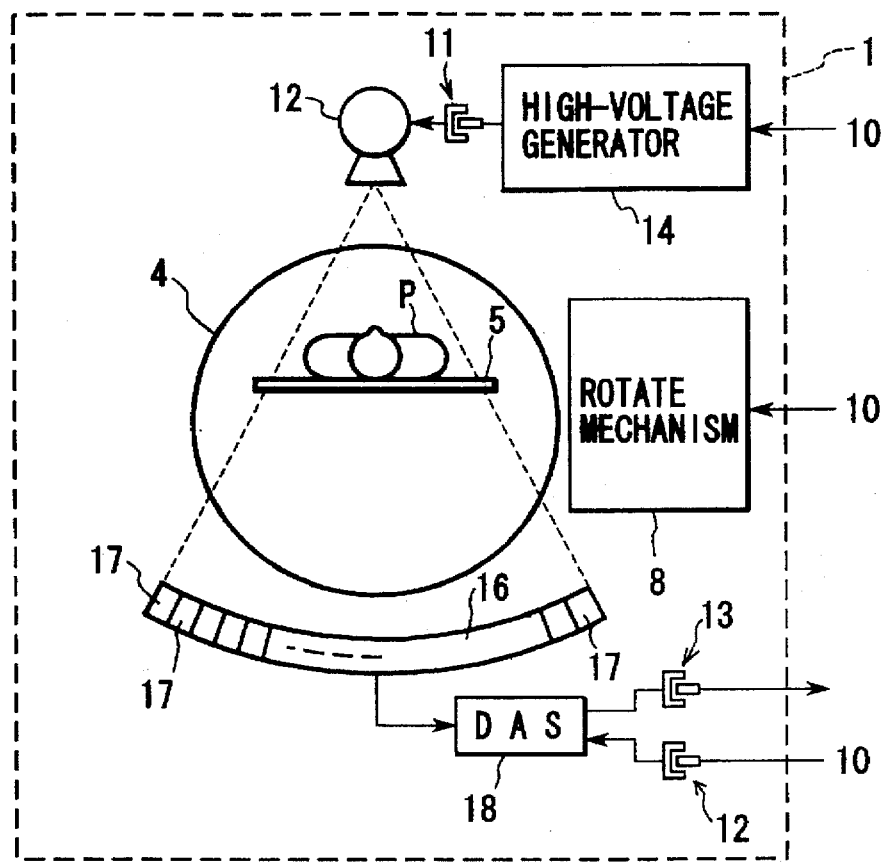
FIG. 4 is a schematic view showing the internal arrangement of a gantry in FIG. 1.

FIG. 3 shows the outer appearance of the computed tomography apparatus according to this embodiment. FIG. 4 shows the schematic internal arrangement of the gantry in FIG. 1. The computed tomography apparatus includes a gantry 1, a couch 2, a console 6, a display 7, and a computer system 20. An opening portion 4 allowing the subject to be inserted is formed in the center of the gantry 1.

The gantry 1 includes an X-ray tube 12, a high-voltage generator 14, a multi-channel type X-ray detector 16, a data acquisition system (DAS) 18, a rotate mechanism 8, slipping mechanisms 11, 12, and 13. Upon application of a high voltage from the high-voltage generator 14, the X-ray tube 12 irradiates a fan-shaped X-ray beam on a subject P.

The multi-channel type X-ray detector 16 has a plurality of detecting elements 17. The detecting elements 17 are arranged substantially in the form of an arc around the focal point of the X-ray tube 12 as the center. Assume that one detecting element corresponds to one channel, and the number of channels of the multi-channel type X-ray detector 16 is "n".

In order to acquire projection data via the multi-channel type X-ray detector 16, the data acquisition system 18 includes n preamplifiers for amplifying detection signals corresponding to the channels, n sample/hold circuits for sampling/holding outputs from the preamplifiers, an analog/digital converter for converting outputs from the sample/hold circuits into digital signals, and a multiplexer for sequentially connecting the sample/hold circuits to the analog/digital converter one by one.

Note that projection data is defined as a set of digital signals simultaneously detected by the detecting elements and corresponding to the first to nth channels.

The rotate mechanism 8 has a rotating ring and a motor. The X-ray tube 12 and the multi-channel type X-ray detector 16 are mounted on the rotating ring to oppose each other through the opening portion 4.

In order to allow concurrent execution of continuous rotation of the rotating ring and a continuous scan operation, the X-ray tube 12 is electrically connected to the high-voltage generator 14 via the slip ring 11, and the data acquisition system 18 is electrically connected to a scan controller 10 via two slip rings 12 and 13.

The couch 2 has a mechanism, a motor, and the like required to manually or electrically slide a tabletop 5. The subject P is placed on the tabletop 5. When the tabletop 5 slides, the subject P enters the opening portion 4 of the gantry 1 together with the tabletop 5.

The console 6 is connected to the computer system 20 to allow the operator to select a slice width, a tube voltage (keV), a tube current (mA), a scan cycle time, a mode, or the like. Note that this apparatus has a real-time mode in which a scan operation and reconstruction of tomographic image data are performed concurrently, and a time sharing mode in which a scan operation and reconstruction of tomographic image data are performed separately. These modes will be described in detail later.

The display 7 is connected to the computer system 20 to display reconstructed tomographic image data.

Figure 5:
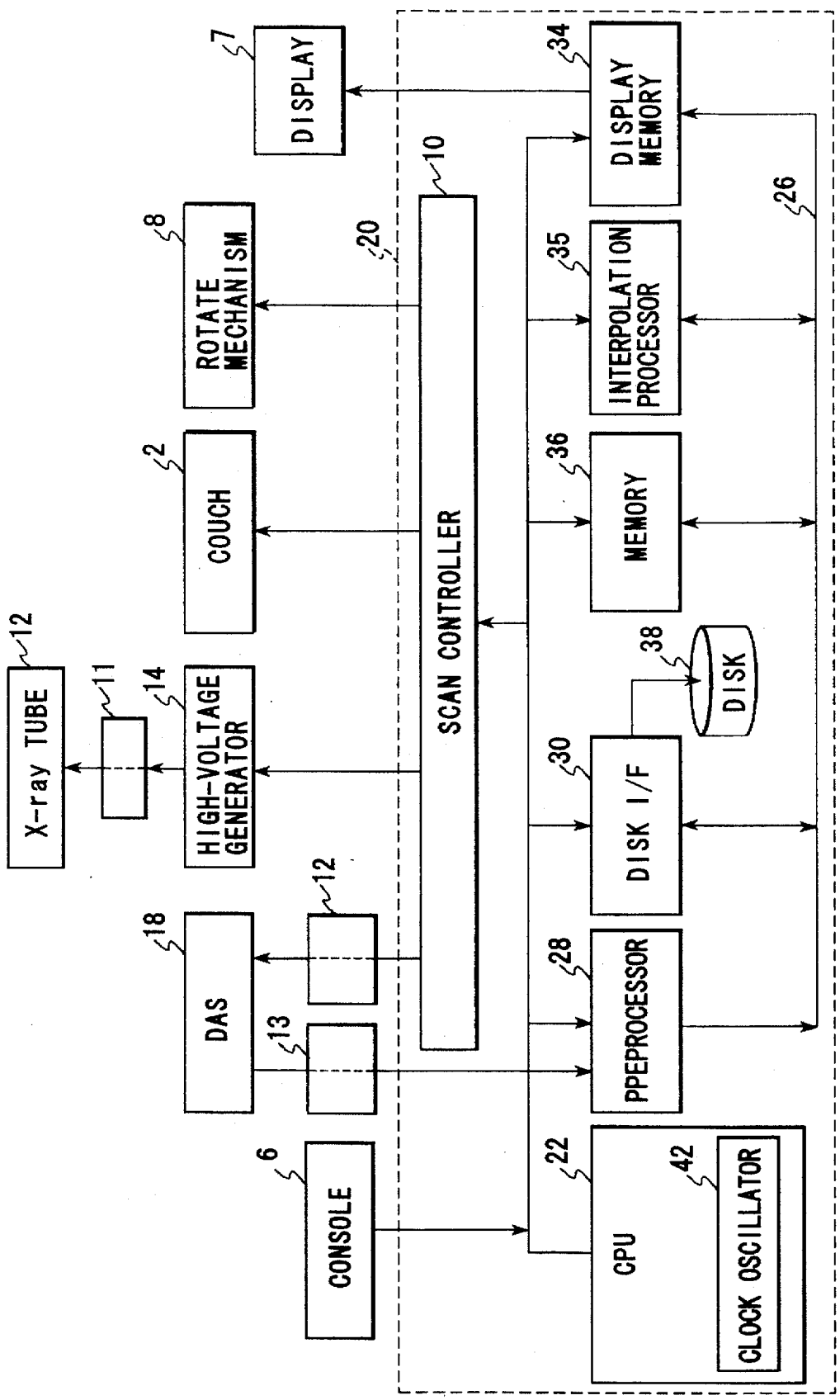
FIG. 5 is a block diagram showing the arrangement of a computer unit in FIG. 1.

FIG. 5 shows the arrangement of the computer system 20. A CPU 22 incorporates a clock oscillator 42, and controls the overall operation of the computer system 20 on the basis of a clock pulse from the clock oscillator 42. The scan controller 10, a preprocessor 28, a disk I/F 30, a memory 36, an interpolation processor 35, a reconstruction processor 32, and a display memory 34 are connected to a control bus 24. The preprocessor 28, the disk I/F 30, the memory 36, the interpolation processor 35, the reconstruction processor 32, and the display memory 34 are connected to a data bus 26. A disk unit 38 is connected to the disk I/F 30. The display 7 is connected to the display memory 34.

The scan controller 10 controls the data acquisition system 18, the high-voltage generator 14, the couch 2, and the rotate mechanism 8.

The preprocessor 28 receives projection data from the data acquisition system 18 via the slip ring 13, and executes preprocessing such as correction of nonuniform sensitivity of the detecting elements with respect to the projection data.

The memory 36 is a rewritable memory such as a DRAM (Dynamic Random Access Memory) or EEPROM (Electrically Erasable and Programmable Read Only Memory), and serves to store reprocessed projection data.

The interpolation processor 35 estimates one projection data set corresponding to a slice position designated by the operator by interpolation (distance interpolation) on the basis of at least two projection data sets repeatedly acquired during at least two revolutions of the X-ray tube 12. That is, the weighted mean of at least two projection data sets acquired at the same rotate angle is calculated in accordance with the distance between the Z-position at which each projection data set has been acquired and the designated Z-position.

The reconstruction processor 32 reconstructs tomographic image data on the basis of the obtained projection data set.

The reconstructed tomographic image data is sent to the display 7 via the display memory 34 to be displayed. The reconstructed tomographic image data is also sent to the disk unit 38 via the disk I/F 30 to be stored in a storage medium such as a magnetic disk.

Figure 6:
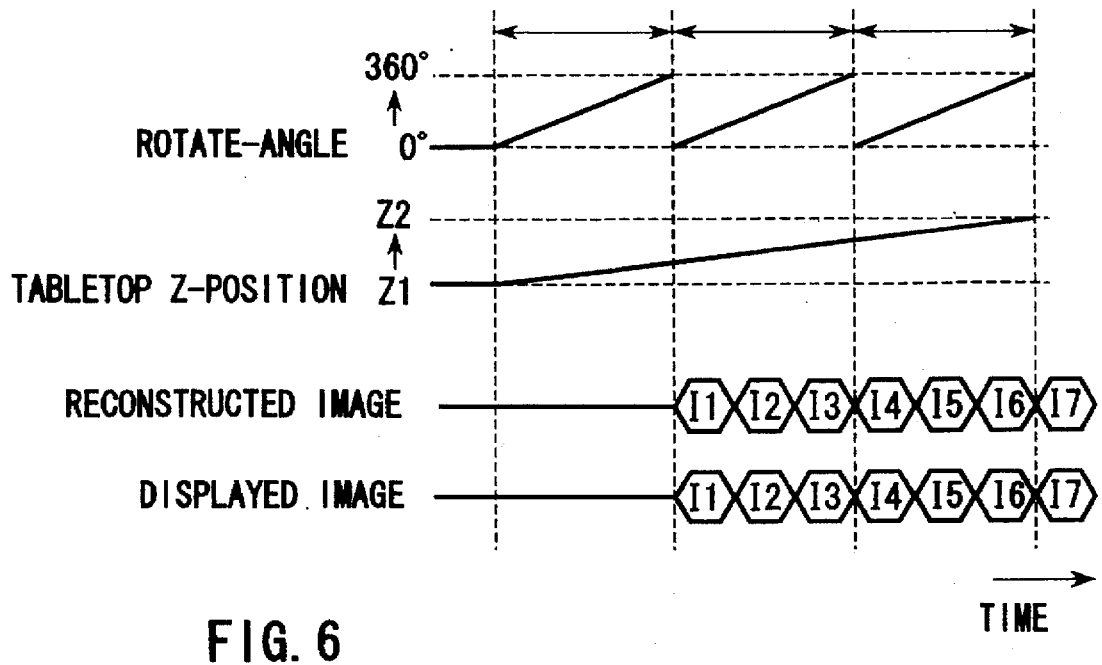
FIG. 6 is a view for explaining a helical scan operation.

FIG. 6 schematically shows a helical scan operation. Assume that the sliding direction of the tabletop 5 is the Z direction, and the position of the tabletop 5 is the Z-position. Assume also that the operator has performed a setting operation to execute a helical scan operation while the tabletop 5 moves from a position Z1 to a position Z2.

The X-ray tube 12 and the multi-channel type X-ray detector 16 are continuously rotated by the rotate mechanism 8. The tabletop 5 of the couch 2 on which the subject is placed is slid at a predetermined speed. A helical scan operation is realized by concurrently causing these two movements.

FIG. 7 shows an operation sequence in the computer system 20. Referring to FIG. 7, steps S1 to S8 correspond to the real-time mode in which a helical scan operation and reconstruction of tomographic image data are concurrently executed, and steps S9 to S13 correspond to the time sharing mode in which reconstruction of tomographic image data is executed after a scan operation. The real-time mode and the time sharing mode are sequentially executed.

First of all, rotation of the X-ray tube 12 and the multi-channel type X-ray detector 16, and sliding of the tabletop 5 are started (step S1). The rotation of the X-ray tube 12 and the multi-channel type X-ray detector 16, and the sliding of the tabletop 5 are continued until the scan operation is completed. When the tabletop 5 reaches the position Z1 (step S2), X-ray radiation and data acquisition are started (step S3). With this operation, acquisition of projection data is started. This acquisition of projection data is repeated at a predetermined period. Acquisition of projection data is defined as an operation of sampling n channel signals at a predetermined period, converting the sampled signals into digital signals, one-dimensionally rearranging the signals, and outputting the resultant signals.

When the X-ray tube 12 rotates once after the start of the acquisition of projection data, acquisition of the first one projection data set is completed. Tomographic image data is reconstructed on the basis of this projection data set (step S4), and the reconstructed tomographic image data is displayed on the display 7.

The time required to reconstruct tomographic image data on the basis of one projection data set required for the reconstruction of one-frame tomographic image data is shorter than that required for acquisition of one projection data set. In addition, the interval between the instant at which one projection data set required for reconstruction of tomographic image data is acquired and the instant at which the tomographic image data reconstructed on the basis of the projection data set is displayed is fixed to a predetermined period of time.

Figure 9:
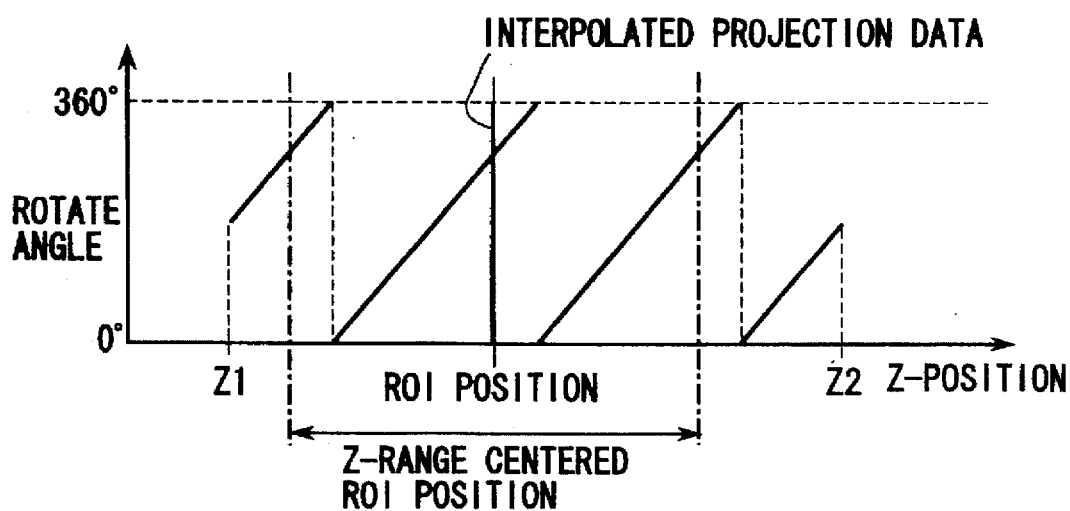
FIG. 9 is a view showing projection data sets used for reconstruction processing in the time sharing mode.

In the time sharing mode (to be described later), as shown in FIG. 9, one projection data set corresponding to the same Z-position is estimated by interpolation on the basis of two projection data sets in the Z-range corresponding to two revolutions of the X-ray tube 12, and tomographic image data is reconstructed on the basis of the one interpolated projection data set.

Figure 8:
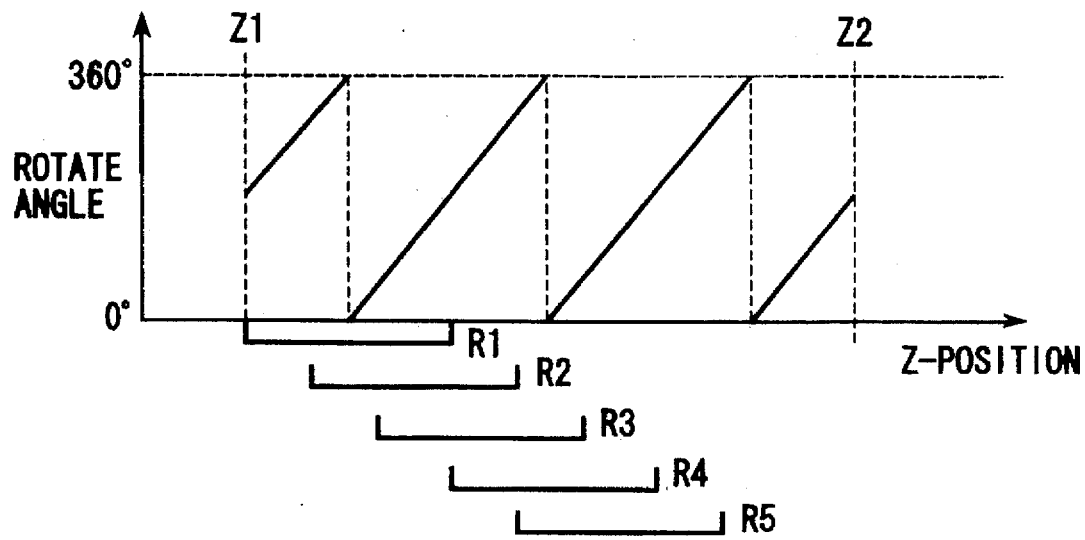
FIG. 8 is a view showing projection data sets used for reconstruction processing in the real-time mode.

In the real-time mode, as shown in FIG. 8, tomographic image data is reconstructed on the basis of one original projection data set in the Z-range (Z1, Z2, Z3, . . . ) corresponding to one revolution of the X-ray tube 12.

That is, in the real-time mode, no interpolation is performed. This means that priority is given to high-speed processing, i.e., real-time processing, over an artifact caused when the Z-position changes within one projection data set. The real-time mode is designed to check, during a scan operation, whether a desired portion is visualized, and hence requires no high-quality images for diagnosis. This mode is based on the fact that the above artifact does not degrade the minimum image quality required to achieve the above object.

As described above, it is important to choose between executing interpolation processing or not executing it in accordance with the mode.

The tomographic image data is repeatedly read out from the display memory 34 and continuously displayed on the display 7 until the next tomographic image data is reconstructed.

In order to faithfully reproduce the speed of movement of an internal organ or the like by matching the real time scale with the display time scale, the interval between the instant at which a projection data set is acquired, e.g., acquisition of a projection data set is completed, and the instant at which tomographic image data reconstructed on the basis of the projection data set is displayed is preferably fixed.

A series of real-time operations in steps S3 to S5, i.e., acquisition of projection data, instantaneous reconstruction of tomographic image data, and display of the tomographic image data, is repeated until the tabletop 5 reaches the position Z2 (step S6), or a scan stop command is input through the console 6 (step S7).

As shown in FIG. 6, every time the X-ray tube 12 rotates through, for example, 120°, immediately preceding tomographic image data is corrected on the basis of projection data acquired during the 120° rotation, and projection data corresponding to 120° rotation before one revolution. With this processing, one-frame tomographic image data can be reconstructed every time the X-ray tube 12 rotates through 120°, thereby greatly improving time resolution as compared with a case wherein tomographic image data is reconstructed on the basis of a projection data set newly acquired every time the X-ray tube 12 rotates through 360°.

When the tabletop 5 reaches the position Z2 (step S6), or a scan stop command is input through the console 6 (step S7), rotation of the X-ray tube 12, sliding of the tabletop 5, X-ray radiation, and acquisition of projection data are stopped. With this operation, the real-time mode is also terminated.

Steps S9 to S13 indicate an operation sequence in the time sharing mode. The time sharing mode is defined as an operation of time-divisionally performing acquisition of projection data and reconstruction of tomographic image data, more specifically, reconstructing tomographic image data by using acquired projection data. The projection data in the range from the position Z1 to the position Z2 have already been acquired and stored in the memory 36.

First of all, the operator inputs a desired Z-position (slice position) to the CPU 22 through the console 6 (step S9). As shown in FIG. 9, at least projection data sets, in the Z-range, which correspond to at least two revolutions of the X-ray tube 12 around the designated slice position as the center are selectively loaded from the memory 36 into the interpolation processor 35 (step S10). One projection data set corresponding to the slice position is estimated by interpolation on the basis of these two projection data sets (step S11). Thereafter, tomographic image data corresponding to the slice position is reconstructed on the basis of the one interpolated projection data set (step S12).

As described above, in the time sharing mode, interpolation processing is executed to reconstruct high-quality tomographic image data having a small artifact. In contrast to this, in the real-time mode, interpolation processing is omitted to increase the processing speed and realize real-time processing. By choosing between executing interpolation processing or not executing it in accordance with the mode in this manner, the real-time mode can be realized in a helical scan operation. Furthermore, in the time sharing mode, a high-quality tomographic image can be obtained.

The present invention is not limited to the embodiment described above, and various modification thereof can be made.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An X-ray computed tomography apparatus comprising:
   acquisition means for repeatedly acquiring projection data associated with a subject by a helical scan operation;
   reconstruction means capable of selecting a first mode of reconstructing tomographic image data on the basis of original projection data acquired by said acquisition means, and a second mode of interpolating the original projection data acquired by said acquisition means, and reconstructing tomographic image data on the basis of the interpolated projection data, and in the first mode, a time required to reconstruct the tomographic image data on the basis of one set of projection data required for reconstruction of one-frame tomographic image data being shorter than a time required for acquisition of the one set of projection data; and
   display means for displaying the reconstructed tomographic image data as a moving image.

2. The apparatus according to claim 1, wherein said display means displays the tomographic image data after a predetermined interval from acquisition of a corresponding one set of projection data in the first mode.

3. The apparatus according to claim 1, wherein said acquisition means comprises an X-ray tube, X-ray detection means arranged to oppose said X-ray tube through the subject, a couch and means for moving at least one of said couch and said X-ray tube relative to the other, the helical scan operation is realized by continuously rotating said X-ray tube around the subject, moving at least one of said couch and said X-ray tube relative to the other, and causing said X-ray detection means to repeatedly acquire projection data at a predetermined period.

4. The apparatus according to claim 3, wherein said reconstruction means reconstructs tomographic image data on the basis of one set of projection data acquired during substantially one revolution of said X-ray tube.

5. The apparatus according to claim 4, wherein said reconstruction means repeatedly reconstructs tomographic image data every time said X-ray tube rotates through a predetermined angle smaller than an angle corresponding to one revolution in the first mode.

6. The apparatus according to claim 3, wherein said reconstruction means comprises means for interpolating set of projection data corresponding to a specific slice position on the basis of at least two sets of projection data acquired during at least two revolutions of said X-ray tube in the second mode.

7. An X-ray computed tomography apparatus comprising:
   acquisition means for acquiring projection data associated with a subject by a helical scan operation;
   interpolation means for interpolating the projection data;
   reconstruction means for reconstructing tomographic image data on the basis of one set of the projection data or interpolated projection data;
   display means for displaying the reconstructed tomographic image data; and
   means for controlling said interpolation means to avoid interpolation of the projection data, when a time required for reconstruction of the tomographic image data is shorter than a time required for acquisition of one set of the projection data.

8. The apparatus according to claim 7, wherein said display means displays the tomographic image data after a predetermined interval from acquisition of one set of corresponding projection data.

9. The apparatus according to claim 7, wherein said acquisition means includes an X-ray tube, and said reconstruction means reconstructs tomographic image data on the basis of one set of the projection data acquired during substantially one revolution of said X-ray tube.

* * * * *